United States Patent [19]

Robota et al.

[11] 4,077,850

[45] Mar. 7, 1978

[54] METHOD FOR THE PURIFICATION OF MONOCHLOROBENZENE

[75] Inventors: Stephen Robota, North Tonawanda; James A. Whelan, Niagara Falls, both of N.Y.

[73] Assignee: Hooker Chemicals & Plastics Corporation, Niagara Falls, N.Y.

[21] Appl. No.: 719,001

[22] Filed: Aug. 30, 1976

[51] Int. Cl.$^2$ .................... B01D 3/34; C07C 25/06
[52] U.S. Cl. .................... 203/29; 260/650 R
[58] Field of Search .................... 260/650 R, 654–656; 203/29, 28, 30–34, 50, 86

[56] References Cited

U.S. PATENT DOCUMENTS

| | | | |
|---|---|---|---|
| 1,741,305 | 12/1929 | Jaeger | 260/650 R |
| 2,707,197 | 4/1955 | Souillard | 260/650 R |
| 3,076,043 | 1/1963 | Dehn | 203/29 |

*Primary Examiner*—Wilbur L. Bascomb, Jr.
*Attorney, Agent, or Firm*—Peter F. Casella; William J. Crossetta, Jr.; Arthur S. Cookfair

[57] ABSTRACT

A method for the purification of monochlorobenzene contaminated with partly chlorinated aliphatic compounds comprises (a) selectively photochlorinating the contaminated monochlorobenzene to convert the partly chlorinated aliphatic compounds to substantially fully chlorinated aliphatic compounds and (b) separating the monochlorobenzene from the more fully chlorinated aliphatic compounds by distillation.

6 Claims, No Drawings

METHOD FOR THE PURIFICATION OF MONOCHLOROBENZENE

BACKGROUND OF THE INVENTION

This invention relates to the purification of monochlorobenzene and in particular to the removal of partly chlorinated aliphatic contaminants from monochlorobenzene.

Monochlorobenzene is commonly employed as an intermediate in the production of various chemical compounds and as a solvent in various chemical manufacturing processes, as well as a solvent or carrier for other chemicals in specific applications such as herbicidal applications. Standards for the use of monochlorobenzene as a solvent for herbicidal use require a relatively pure material containing for example less than 50 parts per million chlorinated aliphatic materials.

Monochlorobenzene produced by direct ring clorination of benzene with chlorine commonly contains up to about 0.4 weight percent perchloroethylene. Monochlorobenzene produced by the oxychlorination of benzene with hydrogen chloride gas and oxygen or air, commonly contains minor amount of chlorinated aliphatics, notably perchloroethylene and to a lesser extent, trichloroethylene, typically in amounts of up to about 2% and about 0.1% by weight respectively. Benzene, dichlorobenzene, and higher chlorinated benzens are also commonly produced as by-products in the production of monochlorobenzene. The latter contaminants, that is benzene, dichlorobenzene, and higher chlorinated benzenes are readily separated from monochlorobenzene by distillation. However, the removal of perchloroethylene from monochlorobenzene presents a specific problem. The relatively volatility of perchloroethylene to monochlorobenzene at low concentration was found to be only 1.4, even though there is a difference of 11.3 degrees Celsius in their boiling points. As a result the separation of this component by distillation requires the use of an expensive high efficiency distillation column with a large number of plates and a high reflux ratio. It is known that perchloroethylene can be separated from monochlorobenzene using an azeotropic agent, such as methanol. However, it has been found that a large excess of methanol, for example, in the amount of 200:1 weight ratio of methanol to perchloroethylene is necessary to achieve an effective azeotropic distillation. The large excess is necessary because monochlorobenzene reduces the perchloroethylene in the methanol-perchloroethylene azeotropic composition. The large excess of methanol increases the heat requirements of the distillation, thereby making this method uneconomical. Other azeotropic agents have been tested and found to demonstrate similar problems to the problem described for methanol.

It is an object of this invention to provide a novel and useful process for the purification of monochlorobenzene and in particular to provide a method for the removal of partly chlorinated aliphatic compounds from monochlorobenzene compositions. It is a further object of this invention to provide a simple and economical process for the removal of perchloroethylene and/or trichloroethylene from monochlorobenzene compositions.

SUMMARY OF THE INVENTION

It has now been found that monochlorobenzene compositions contaminated with partly chlorinated aliphatic compounds may be effectively and economically purified by a process comprising (A) the selective photochlorination of the partly chlorinated aliphatic compounds to produce more fully chlorinated aliphatic compounds and (B) the separation of the more fully chlorinated compounds from the monochlorobenzene by distillation. More particularly, it has been found that monochlorobenzene contaminated with perchloroethylene and/or trichloroethylene can be purified by selective photochlorination and subsequent distillation. It has been found surprisingly that during the photochlorination of such contaminated monochlorobenzene compositions, trichloroethylene may be readily converted to pentachloroethane and perchloroethylene to hexachloroethane with little or no concommitant formation of higher chlorinated benzenes. Pentachloroethane (b.p. 162.0° C.) and hexachloroethane (b.p. 185.5° C.) are readily separated from the monochlorobenzene (b.p. 132.1° C.) by distillation. The photochlorination step may be effected in a known manner either batchwise or continuously by the addition of chlorine gas to the impure monochlorobenzene composition and exposure of this reaction mixture to actinic radiation. The photochlorination reaction is carried out for a period of time sufficient to effect the desired conversion of the partly chlorinated aliphatic compounds present to more fully chlorinated aliphatic compounds. During the substantially complete conversion of partly chlorinated aliphatic compounds in this manner, little or no formation of higher chlorinated benzenes occurs. Partly chlorinated aliphatic compounds that may be converted and separated from monochlorobenzene in this manner include especially, partly chlorinated branched or straight chain lower aliphatic compounds and most especially unsaturated lower aliphatic compounds, of up to about twenty carbon atoms. The process of this invention is especially effective in, and is particularly directed to, the purification of monochlorobenzene compositions containing minor amounts, typically less than about ten percent by weight, of perchloroethylene and/or trichloroethylene, most especially perchloroethylene. Thus, for example, an impure monochlorobenzene composition, containing a minor amount of perchloroethylene, may be selectively photochlorinated until substantially all of the perchloroethylene is converted to hexachloroethane, or until the amount of perchloroethylene has been reduced to a desirably low level, such as below about 50 ppm, by conversion to hexachloroethane, with little or no formation of higher chlorinated benzenes. The degree of completion of the photochlorination step, for example, the degree of conversion of perchloroethylene to hexachloroethane and/or conversion of trichloroethylene to pentachloroethane is readily determined, or may be continuously monitored, by conventional analytical techniques, such as gas chromotographic techniques.

The actinic radiation suitable for the photochlorination step is preferably of a wavelength of about 2500 to about 5000 A, and most preferably of about 2600 A to about 4000 A. Suitable known light sources which may be employed for this purpose include, for example, tungsten filament lamps, ultraviolet lamps, mercury vapor arc lamps, fluorescent lamps and the like. The photochlorination step is carried out in a known manner, the amount of time required for photochlorination being dependent upon the light intensity, chlorine concentration, depth of light penetration, and the degree of mixing provided.

It has been found that the presence of iron tends to catalyze the formation of dichlorobenzene during the photochlorination step. Thus, it is desirable that the monochlorobenzene composition be kept free from iron or that iron be present only at very low ppm concentrations in order to minimize the formation of dichlorobenzene. For this reason it is preferred that the photochlorination be carried out in a reactor made of glass, nickel, or other non-iron contributing material of construction.

The following specific examples are set forth to further illustrate this invention in the manner in which it may be practiced. It is to be understood that the specific details set forth in the examples have been chosen for the purpose of illustration and are not intended to limit the invention. In the examples unless otherwise indicated, all parts and percentages are by weight and all temperatures are in ° Celsius. All of the analytical results set forth in the examples were obtained by gas chromatography. Using this method it was found that perchloroethylene was detectable at 50 ppm but undetectable at 25 ppm. All of the reactions were conducted at atmospheric pressure.

EXAMPLE 1

To an impure monochlorobenzene sample having a composition as set forth below was added 5% by weight chlorine. Fifty-five parts by weight of the chlorine-containing sample were placed in a Pyrex glass test tube 1 in. in diameter × 4 in. long and exposed to radiation from 100 watt ultraviolet light placed outside the reaction tube. During the reaction samples were withdrawn periodically and analyzed by gas chromatography. After 2.5 minutes all the perchloroethylene reacted to form hexachloroethane. The reaction started at room temperature (21° C.); by the end of the reaction the temperature had increased to 132° C. from the heat of the ultraviolet light. The reactant feed and product analysis in weight percent were as follows:

|  | COMPOSITION (weight percent) | |
| --- | --- | --- |
|  | Reactant Feed | Product |
| Unknown | 0.1 | .027 |
| Benzene | Non-detectable | .0025 |
| Perchloroethylene | 1.09 | Non-detectable |
| Monochlorobenzene | 98.87 | 98.20 |
| Dichlorobenzenes | .03 | .036 |
| Hexachloroethane | Non-detectable | 1.61 |

EXAMPLE 2

A continuous stream of impure monochlorobenzene was mixed with about 5 percent by weight of chlorine and passed through a 3.0 in. diameter Pyrex glass tubular reactor at a flow rate of about 6 milliliters per minute. A 0.25 in. section of the tube was exposed to the light of two 100 watt ultraviolet lamps. During a five minute reaction period the temperature of the reaction mixture rose from 21° C. to a maximum of 40° C. The reactant feed and product analysis were as follows:

|  | COMPOSITION (weight percent) | |
| --- | --- | --- |
|  | Feed | Product |
| Unknown | Non-detectable | .004 |
| Benzene | Non-detectable | .027 |
| Perchloroethylene | 1.5 | Non-detectable |
| Monochlorobenzene | 98.5 | 97.70 |
| Dichlorobenzene | Non-detectable | .029 |
| Hexachloroethane | Non-detectable | 2.24 |

EXAMPLE 3

To determine the effectiveness of the present invention in the conversion of trichloroethylene to pentachloroethane, a stream of monochlorobenzene containing both perchloroethylene and trichloroethylene was selectively photochlorinated following the procedure of Example 2, until the trichloroethylene content was substantially less than 50 ppm. The feed and product analysis were as follows:

|  | COMPOSITION (weight percent) | |
| --- | --- | --- |
|  | Feed | Product |
| Unknown | Non-detectable | .002 |
| Trichloroethylene | .21 | .003 |
| Perchloroethylene | .50 | .035 |
| Benzene | .027 | .027 |
| Monochlorobenzene | 96.73 | 96.44 |
| Hexachlorobenzene | 1.31 | 1.98 |
| Pentachloroethane | 1.2 | 1.49 |
| Dichlorobenzenes | .019 | .028 |

EXAMPLE 4

Following the procedure of Example 2, several samples of a commercial grade monochlorobenzene were photochlorinated. The samples treated were a perchloroethylene-contaminated monochlorobenzene produced commercially by oxychlorination of benzene. Typical feed and product analysis were as follows:

|  | COMPOSITION (weight percent) | |
| --- | --- | --- |
|  | Feed | Product |
| Unknown | .38 | .167 |
| Perchloroethylene | 1.23 | Non-detectable |
| Benzene | 9.87 | 7.38 |
| Monochlorobenzene | 88.51 | 90.68 |
| Hexachloroethane | Non-detectable | 1.74 |
| Dichlorobenzenes | .002 | .032 |

EXAMPLE 5

A commercial grade sample of monochlorobenzene, containing about 1.63 weight percent perchloroethylene, was photochlorinated in an annular photochlorination reactor designed for continuous flow and recirculation of reactants around a centrally-positioned 100 watt ultraviolet lamp enclosed in a Pyrex glass tube. The reactor was constructed of an iron-free nickel material (to prevent contamination from iron and consequent ring chlorination). The monochlorobenzene was continuously re-circulated through the reactor to provide a total of 4.35 minutes residence time of exposure to the ultraviolet radiation. During the reaction the temperature of the monochlorobenzene stream rose from 21° C. to 36° C. The reactant feed and product analysis were as follows:

|  | COMPOSITION (weight percent) | |
| --- | --- | --- |
|  | Feed | Product |
| Low Boilers | Non-detectable | .034 |
| Perchloroethylene | 1.63 | Non-detectable |
| Benzene | .041 | .029 |
| Monochlorobenzene | 98.18 | 97.68 |
| Hexachloroethane | Non-detectable | 2.29 |
| Paradichlorobenzene | .02 | .26 |
| Orthodichlorobenzene | Non-detectable | .15 |

In all of the foregoing examples, the amounts of hexachloroethane and pentachloroethane produced by the photochlorination was in stoichiometric proportion to the amount of contaminant present, namely perchloroethylene and trichloroethylene, respectively. From the photochlorinated product of the foregoing examples, hexachloroethane and pentachloroethane as well as higher chlorinated benzenes are readily separated from the monochlorobenzene by conventional distillation procedures.

EXAMPLE 6

The product of Example 5 was distilled using a 20 plate column and a reflux ratio of 2:1 to remove the monochlorobenzene from the hexachloroethane and higher chlorinated benzenes and provide a purified monochlorobenzene product having a composition as shown below:

|  | COMPOSITION (weight percent) | |
|---|---|---|
|  | Feed | Product |
| Low Boilers | .034 | .087 |
| Perchloroethylene | Non-detectable | Non-detectable |
| Benzene | .029 | .028 |
| Monochlorobenzene | 97.28 | 99.869 |
| Hexachloroethane | 2.29 | Non-detectable |
| Paradichlorobenzene | .26 | .0016 |
| Orthodichlorobenzene | .15 | Non-detectable |
| High Boilers | Non-detectable | .014 |

We claim:

1. A method of purifying monochlorobenzene contaminated with partly chlorinated unsaturated lower aliphatic compounds comprising
   (A) selectively photochlorinating the chlorinated unsaturated aliphatic compounds to produce more fully chlorinated saturated aliphatic compounds, and
   (B) separating monochlorobenzene from the more fully chlorinated compounds by distillation.

2. A method according to claim 1 wherein the partly chlorinated aliphatic compounds are selected from perchloroethylene, trichloroethylene, and mixtures thereof.

3. A method according to claim 2 wherein perchloroethylene is photochlorinated to produce hexachloroethane.

4. A method according to claim 2 wherein trichloroethylene is photochlorinated to produce pentachloroethane.

5. A method according to claim 1 wherein the method is carried out in a photochemical reactor in an environment substantially of iron metal.

6. A method according to claim 1 wherein (A) a monochlorobenzene composition contaminated with perchloroethylene is selectively photochlorinated to convert the perchloroethylene to hexachloroethane until less than about 50 parts of perchloroethylene per million parts of monochlorobenzene remain, and (B) the monochlorobenzene is separated by distillation.

* * * * *

UNITED STATES PATENT OFFICE
CERTIFICATE OF CORRECTION

Patent No. 4,077,850          Dated March 7, 1978

Inventor(s) Stephen Robota and James A. Whelan

It is certified that error appears in the above-identified patent and that said Letters Patent are hereby corrected as shown below:

Claim 5, line 22, "substantially of" should read ---substantially free of---.

*Signed and Sealed this*

*Twenty-fourth* Day of *October 1978*

[SEAL]

Attest:

RUTH C. MASON
*Attesting Officer*

DONALD W. BANNER
*Commissioner of Patents and Trademarks*